United States Patent [19]
Berns et al.

[11] Patent Number: 5,789,215
[45] Date of Patent: Aug. 4, 1998

[54] GENE TARGETING IN ANIMAL CELLS USING ISOGENIC DNA CONSTRUCTS

[75] Inventors: Anton Berns, Spaarndam; Els Robanus Maandag, Haarlem; Hein te Riele, Amsterdam, all of Netherlands

[73] Assignee: GenPharm International, San Jose, Calif.

[21] Appl. No.: 908,348

[22] Filed: Aug. 7, 1997

Related U.S. Application Data

[63] Continuation of Ser. No. 700,324, Aug. 8, 1996, abandoned, which is a continuation of Ser. No. 563,138, Nov. 27, 1995, abandoned, which is a continuation of Ser. No. 216,121, Mar. 22, 1994, abandoned, which is a continuation of Ser. No. 748,342, Aug. 20, 1991, abandoned.

[51] Int. Cl.$^6$ .............................. C12N 5/06; C12N 15/00; C12N 15/09; C12N 15/11
[52] U.S. Cl. ...................... 435/172.3; 435/172.1; 435/320.1; 435/325; 435/326; 800/2; 935/56; 935/70; 935/71; 935/34; 935/53
[58] Field of Search ................. 435/172.1, 172.3, 435/320.1, 325, 326; 800/2; 935/50, 56, 34, 53, 70, 71, 83, 84

[56] References Cited

FOREIGN PATENT DOCUMENTS

| 9011354 | 4/1990 | WIPO . |
| 9101140 | 2/1991 | WIPO . |
| 9106667 | 5/1991 | WIPO . |

OTHER PUBLICATIONS

G. Bain et al., *Cell*, vol. 79, 1994, pp. 885–892.
J. Charron et al., *Molecular and Cellular Biology*, vol. 10, No. 4, 1990, pp. 1799–1804.
C. Deng and M.R. Capecchi, *Molecular and Cellular Biology*, vol. 12, No. 8, 1992, pp. 3365–3371.
C. Deng et al., *Molecular and Cellular Biology*, vol. 13, No. 4, 1993, pp. 2134–2140.
B. Koller et al., *Proc. Natl. Acad. Sci. USA*, vol. 88, 1991, pp. 10730–10734.
A.H. Schinkel et al., *Cell*, vol. 77, 1994, pp. 491–502.
J. van Deursen and B. Wieringa, *Nucleic Acids Research*, vol. 20, No. 15, 1992, pp. 3815–3820.
van der Lugt et al., *Genes & Development*, vol. 8, 1984, pp. 757–769.
H. Zheng and E. Wilson, *Nature* vol. 344, 1990, pp. 170–173.
Adair et al., *Proc. Natl. Acad. Sci. USA* 86:4574–4578 (1989).
Bollag et al., *Annual Review of Genetics* 23:199–225 (1989).
Jasin and Berg, *Genes & Development* 2:1353–1363 (1988).
Joyner et al., *Nature* 338:153–156 (1989).
Mansour et al., *Nature* 336:348–352 (1988).
Sedivy and Sharp, *Proc. Natl. Acad. Sci. USA* 86:227–231 (1989).
Shen and Huang, *Genetics* 112:441–457 (1986).
Song et al., *Proc. Natl. Acad. Sci. USA* 84:6820–6824 (1987).
Soriano et al., *Cell* 64, 693–702 (1991).
Swebilius Singer et al., *Cell* 31:25–33 (1981).
Waldman and Liskay, *Molecular and Cellular Biology* 8:5350–5357 (1988).
Watt et al., *Proc. Natl. Acad. Sci. USA* 82:4768–4772 (1985).
Zijlstra et al., *Nature* 342:435–438 (1989).
Zimmer et al., *Nature* 338:150–153 (1989).
Lowy et al. 1980 *Cell* 22:817–823.
Charron et al. (1990) Molecular: Cellular Biology 10(4): 1799–1805.
Fell et al. (1989) PNAS, USA 86: 8507–8511.
Cruz et al. (1990) *Nature* 348:171–173.
Schwartzberg et al. (1989). *Science* 246:799–803.
Baker et al., (1988). Molecular and Cellular Biology 8(10): 4041–4047.
ten Asbroek et al. 1990. *Nature* 348:174–175.
Rubinitz et al. 1984. Mol. Cell. Biol. 4(11): 2253–2258.
Van der Lugt, N., et al.. *Gene*, 105:263–267 (1991).
Te Riele, H., et al., *Nature* 348:649–651 (1990).
Hooper, M., et al., *Nature* 326:292–295 (1987).
Yenofsky, R., et al., *Proc. Natl. Acad. Sci. (U.S.A.)* 87:3435–3439 (1990).
Waldman, A.S. and Liskay, R.M., *Proc. Natl. Acad. Sci. (U.S.A.)* 4:5340–5344 (1987).
Camerini–Otero & Kucherland, *The New Biologist* 4:337–341 (1990).
Doetschman et al., *Proc. Natl. Acad. Sci. (U.S.A.)* 85:8583–8587 (1988).
Doetschman et al., *Nature* 330:576–578 (1988).
Thomas et al., *Cell* 44:419–428 (1986).
Koller et al., *Proc. Natl. Acad. Sci. (U.S.A.)* 86:8927–8931 (1989).
Smithies et al., *Nature* 317:230–234 (1985).
Thomas & Capecchi, *Cell* 51:503–512 (1987).

*Primary Examiner*—Brian R. Stanton
*Attorney, Agent, or Firm*—Townsend & Townsend & Crew

[57] ABSTRACT

The present invention provides novel methods for modifying the genome of an animal cell which typically comprise the steps of: constructing a DNA molecule in which desired sequence modifications are contained in a segment of DNA (a "targeting DNA") that is substantially isogenic with a DNA in the cell genome (a "target DNA"); introducing the targeting DNA construct into the cell (e.g., by microinjection, electroporation, transfection, or calcium phosphate precipitation); and selecting cells in which the desired sequence modifications have been introduced into the genome via homologous recombination.

18 Claims, 2 Drawing Sheets

GENE TARGETING IN ANIMAL CELLS USING ISOGENIC DNA CONSTRUCTS

This is a Continuation of application Ser. No. 08/700,324, filed Aug. 8, 1996, now abondoned, which is a continuation of application Ser. No. 08/563,138, filed Nov. 27, 1995, now abandoned, which is a continuation of application Ser. No. 08/216,121, filed Mar. 22, 1994, now abandoned, which is a continuation of application Ser. No. 07/748,342, filed Aug. 20, 1991, now abandoned, the disclosure of which is incorporated by reference.

FIELD OF THE INVENTION

The present invention relates generally to methods for modifying the genome of animal cells, including human cells, and more particularly, to methods for modifying a genomic DNA sequence by homologous recombination using substantially isogenic DNA constructs.

BACKGROUND OF THE INVENTION

Targeted gene disruption by homologous recombination has met with variable success in higher eukaryotes. While it has been possible to isolate cells which have stably incorporated exogenously prepared DNA sequences, in the vast majority of these cells, the DNA has integrated randomly into the genome rather than at the desired target site via homologous recombination. The ratio of the number of homologous recombinants to the total number of integration events varies, but typically, when there is no direct selection or enrichment for homologous recombinants, less than 1% of the integration events result from homologous recombination and ratios as low as 1 in 40,000 have been observed. Variations in the relative targeting efficiency have not been clearly attributable to differences in the length of homologous sequence present in the targeting constructs. Nor has any unequivocal correlation been documented between recombination efficiency and transcriptional activity of the target gene or chromosomal location of the target gene.

If the homologous recombinants can only be obtained amidst a large background of random integration events, then it may be impractical, if not impossible, to effectively target many genomic sequences. The approaches taken to overcoming this problem have focused on developing special strategies to screen or select homologous recombinants from the large background of non-homologous or random integration events. In a few situations in which the targeted gene is itself a dominant selectable marker, it may be feasible to select directly for homologous recombinants. For example, knocking out the hprt gene (encoding hypoxanthine phosphoribosyl transferase) results in increased tolerance of the base analog 6-thioguanine (Thomas, K. and M. Capecchi, Cell 51:503–512 (1987). However, such particularized methods are not widely applicable. Other selection procedures aim at the enrichment for the desired homologous recombination event by suppressing colony formation due to random integrations of the targeting construct. In single selection protocols, the targeting constructs contain a marker gene, typically conferring drug resistance, deprived of transcriptional and/or translational start signals, in such a way that the juxtaposition of the marker gene and functional expression signals would be obtained on homologous recombination but only rarely on random integration. Sedivy, J., and P. Sharp, Proc. Nat'l Acad. Sci. USA 86:227–231 (1989). The double or "positive/negative" selection procedure developed by Capecchi and co-workers makes use of an autonomously expressed marker gene, but the targeting construct is flanked by a second gene which is detrimental to the cell and which tends to be lost on homologous recombination but not on random integration. Mansour, S., at al., Nature 336:348–352 (1988).

Another approach has involved the use of screening procedures based on the polymerase chain reaction ("PCR"), in which pools of cells are tested for potential homologous recombinants using pairs of primers which will be juxtaposed only if homologous recombination has occurred. Any pools containing potential homologous recombinants are then sub-divided and the procedure is continued until a small enough pool of cells can be analyzed individually. Zimmer, A., et al., Nature 338:150–153 (1989); and Joyner, A., et al., Nature 338:153–156 (1989). Besides the labor involved in screening, the PCR protocols also require that appropriate regions of the DNAs have been sequenced and that oligonucleotide primers be obtained.

The relative inefficiency of homologous recombination is even more problematic when working with cells that are not easily reproduced in vitro and for which the aforementioned selection and screening protocols may be impractical, if not impossible. For example, there are a large variety of cell types, including many stem cell types, which are difficult or impossible to clonally reproduce in vitro. If the relative frequency of homologous recombination itself could be improved, then it might be feasible to target a variety of cells which are not amenable to specialized isolation techniques such as positive/negative selection or PCR screening. (See, WO91/01140, which is incorporated herein by reference.)

Thus, there remains a significant need for gene targeting systems in which homologous recombinants can be routinely and efficiently obtained at a high enough frequency to obviate the necessity of special selection and screening protocols. The present invention fulfills these and other needs.

SUMMARY OF THE INVENTION

The present invention provides novel methods for modifying the genome of an animal cell comprising the steps of: constructing a DNA molecule in which desired sequence modifications are contained in a segment of DNA (a "targeting DNA") that is substantially isogenic with a DNA in the cell genome (a "target DNA"); introducing the targeting DNA construct into the cell (e.g., by microinjection, electroporation, transfection, or calcium phosphate precipitation); and selecting cells in which the desired sequence modifications have been introduced into the genome via homologous recombination.

Preferably, the targeting DNA will be derived from a cell line that is closely related to the cell line which is being targeted; so that the sequence of the targeting DNA is substantially identical with the sequence of the target DNA (except for the desired sequence modifications). By using substantially isogenic targeting DNA, a substantial fraction of the cells in which integration has occurred will have undergone homologous recombination between the targeting DNA sequence and the target DNA sequence. Since the integration events are thereby enriched for homologous recombinants, it is possible to forego the use of special selection and screening protocols used to isolate rare homologous recombinants from a large background of non-homologous integration events.

Although the present invention has been applied to laboratory mice strains such as BALB/c and 129, the invention will be even more useful for gene targeting in non-murine animals. The typical mouse strains used in laboratories tend to be fairly inbred and, as a result, there is smaller likelihood of sequence divergence in an allele derived from different lines (see, e.g., Bishop, C., et al., Nature 315:70–72 (1985)). In contrast, many other animals are not so inbred, and there is a greater chance of sequence divergence between alleles derived from different individuals. The restriction fragment length polymorphisms ("RFLPs"), useful in "fingerprinting" human DNA, are an example of this phenomenon in a non-inbred species.

A preferred cell type for targeting the genome of a mammalian organism is the embryonic stem cell. Preferably, the DNA construct contains an antibiotic resistance marker and the cells are first selected on a medium containing the antibiotic.

The present invention also provides novel methods for creating genetically modified animals comprising the steps of: modifying the genome of embryonic stem cells derived from the animal, as described above; introducing the modified embryonic stem cells into blastocysts derived from the same species of animal; and using a pseudo-pregnant female to carry the chimeric animal to term. The resulting chimeric animal can in turn be bred to obtain non-chimeric animals in which the desired genetic alteration has been stably inherited through germ-line transmission.

The present invention can also be used for the direct targeting of animal zygotes. The targeting DNA can be introduced by, for example, microinjection, and then, with mammals for example, the modified zygotes can be transferred to pseudo-pregnant females capable of carrying the animal to term. Similarly, for somatic gene therapy, the genome of somatic cells of an animal is directly modified using the substantially isogenic targeting DNA and then the modified cells are introduced into the same or a different animal.

In another aspect, the present invention provides cells exhibiting a recombination event at a preselected native target DNA site in the cell genome. Thus, in view of the increased efficiency of recombination utilizing the methods of the present invention, a collection of cells having undergone a recombination event will exhibit between about 10–90%, typically at least about 30 to 50%, recombination. The cells exhibiting the desired characteristics may be selected for and isolated in accordance with standard techniques, and grown into animals.

DETAILED DESCRIPTION OF THE INVENTION

Figure 1A:
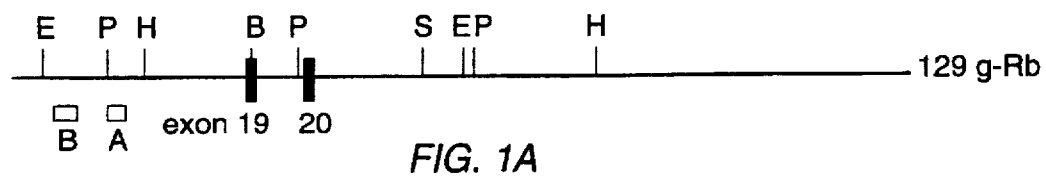
FIG. 1. DNA targeting constructs. (a) The retinoblastoma (Rb) locus around exons 19 and 20 (black boxes), in mouse strain 129. Restriction enzyme sites are as follows: B=BglII, E=EcoRI, H=HindIII, Hp=HpaI, P=PstI, and S=StuI. Except for the StuI site, these sites are also present in the corresponding BALB/c region. (b) The DNA targeting constructs containing the neo gene inserted into the BglII site of exon 19 within a 10.5 kb Rb HpaI fragment derived from mouse strains 129 (targeting construct "129Rb-neo") or BALB/c (targeting construct "B/cRb-neo"). The neo marker was flanked by 2.5 and 8 kb of Rb sequence. (c) and (d). Two additional isogenic targeting constructs generated by inserting the hprt-minigene (Van der Lugt, N., et al., Gene, (1991)) or the hyq gene (Te Riele, H., et al., Nature 348:649–651 (1990)) into the BglII site of exon 19 within a 17 kb 129-derived Rb fragment, giving 129Rb-hprt (c) and 129Rb-hyg (d), respectively. These two constructs were flanked by non-endogenous SalI sites. A and B indicate fragments used as probes to detect modifications at Rb.

In accordance with the present invention, gene targeting can be used to modify the genome of animal cells, including human cells, using an efficient technique involving homologous recombination between substantially isogenic DNA constructs. By introducing an exogenous "targeting DNA" into eukaryotic cells, selecting for cells in which the targeting DNA has been stably integrated into the recipient cell genome is readily accomplished. The methods provided for substantially increased frequency of recombination, one to three orders of magnitude higher, or more are pending upon the target and protocol.

There are two general events believed to be responsible for stable integration. In homologous recombination, the incoming DNA interacts with and integrates into a site in the genome that contains a substantially homologous DNA sequence. In non-homologous ("random" or "illicit") sequence. In non-homologous ("random" or "illicit") integration, the incoming DNA is not found at a homologous sequence in the genome but integrates elsewhere, apparently at one of a large number of potential locations. In general, studies with higher eukaryotic cells have revealed that the frequency of homologous recombination is far less than the frequency of random integration. The ratio of these frequencies has direct implications for "gene targeting" which depends on integration via homologous recombination (i.e. recombination between the exogenous "targeting DNA" and the corresponding "target DNA" in the genome).

Gene targeting represents a major advance in the ability to selectively manipulate animal cell genomes. Using this technique, a particular DNA sequence can be targeted and modified in a site-specific and precise manner. Different types of DNA sequences can be targeted for modification, including regulatory regions, coding regions and regions of DNA between genes. Examples of regulatory regions include: promoter regions, enhancer regions, terminator regions and introns. By modifying these regulatory regions, the timing and level of expression of a gene can be altered. Coding regions can be modified to alter, enhance or eliminate, for example, the specificity of an antigen or antibody, the activity of an enzyme, the composition of a food protein, the sensitivity of protein to inactivation, the secretion of a protein, or the routing of a protein within a cell. Introns and exons, as well as inter-genic regions, are suitable targets for modification.

Modifications of DNA sequences can be of several types, including insertions, deletions, substitutions, or any combination of the preceding. A specific example of a modification is the inactivation of a gene by site-specific integration of a nucleotide sequence that disrupts expression of the gene product. Using such a technique to "knock out" a gene by targeting will avoid problems associated with the use of antisense RNA to disrupt functional expression of a gene product. For example, one approach to disrupting a target gene using the present invention would be to insert a selectable marker into the targeting DNA such that homologous recombination between the targeting DNA and the target DNA will result in insertion of the selectable marker into the coding region of the target gene.

It may be preferable to incorporate a selectable marker into the targeting DNA which allows for selection of targeted cells that have stably incorporated the targeting DNA. This is especially useful when employing relatively low efficiency transformation techniques such as electroporation, calcium phosphate precipitation and liposome fusion, as discussed below, where typically fewer than 1 in 1000 cells will have stably incorporated the exogenous DNA. Using high efficiency methods, such as microinjection into nuclei, typically from 5–25% of the cells will have incorporated the targeting DNA; and it is therefore feasible to screen the targeted cells directly without the necessity of first selecting for stable integration of a selectable marker.

Examples of selectable markers include: genes conferring resistance to compounds such as antibiotics, genes conferring the ability to grow on selected substrates, genes encoding proteins that produce detectable signals such as luminescence. A wide variety of such markers are known and available, including, for example, antibiotic resistance genes such as the neomycin resistance gene (neo), Southern, P., and P. Berg, *J. Mol. Appl. Genet.* 1:327–341 (1982); and the hygromycin resistance gene (hyg), *Nucleic Acids Research* 11:6895–6911 (1983), and Te Riele, H., et al., *Nature* 348:649–651 (1990). Selectable markers also include genes conferring the ability to grow on certain media substrates such as the tk gene (thymidine kinase) or the hprt gene (hypoxanthine phosphoribosyltransferase) which confer the ability to grow on HAT medium (hypoxanthine, aminopterin and thymidine); and the bacterial gpt gene (guanine/xanthine phosphoribosyltransferase) which allows growth on MAX medium (mycophenolic acid, adenine, and xanthine). See Song, K.-Y., et al. *Proc. Nat'l Acad. Sci. U.S.A.* 84:6820–6824 (1987). Other selectable markers for use in mammalian cells, and plasmids carrying a variety of selectable markers, are described in Sambrook, J., et al., *Molecular Cloning—A Laboratory Manual*, Cold Spring Harbor Laboratory, Cold Spring Harbor, N.Y. (1989) (hereinafter "Sambrook"), see chapter 16.

If a selectable marker is used, the preferred location of the marker gene in the targeting construct will depend on the aim of the gene targeting. For example, if the aim is to disrupt target gene expression, then the selectable marker can be cloned into targeting DNA corresponding to coding sequence in the target DNA. Alternatively, if the aim is to express an altered product from the target gene, such as a protein with an amino acid substitution, then the coding sequence can be modified to code for the substitution, and the selectable marker can be placed outside of the coding region, in a nearby intron for example.

If the selectable markers will depend on their own promoters for expression and the marker gene is derived from a very different organism than the organism being targeted (e.g. prokaryotic marker genes used in targeting mammalian cells), it is preferable to replace the original promoter with transcriptional machinery known to function in the recipient cells. A large number of transcriptional initiation regions are available for such purposes including, for example, metallothionein promoters, thymidine kinase promoters, beta-actin promoters, immunoglobulin promoters, SV40 promoters and human cytomegalovirus promoters. A widely used example is the pSV2-neo plasmid which has the bacterial neomycin phosphotransferase gene under control of the SV40 early promoter and confers in mammalian cells resistance to G418 (an antibiotic related to neomycin). Southern, P., and P. Berg, *J. Mol. Appl. Genet.* 1:327–341 (1982). A number of other variations may be employed to enhance expression of the selectable markers in animal cells, such as the addition of a poly(A) sequence (see, e.g., Thomas, K., et al., *Cell* 44:419–428 (1986)); and the addition of synthetic translation initiation sequences (see, e.g., Thomas, K. and M. Capecchi, *Cell* 51:503–512 (1987)). Both constitutive and inducible promoters may be used.

In some cases, it may be desirable for the modification sequences (including selectable markers) to alter the transcriptional activity of the target gene. However, if selectable markers are used and it is not desirable to affect transcriptional activity of the target gene, it will be preferable to use selectable markers with an inducible promoter and/or to include a transcription termination sequence downstream of the selectable marker. A variety of inducible promoters and transcription termination sequences are known and available. See, e.g., Sambrook, supra.

Where the target gene is highly expressed or readily inducible, it may be advantageous to use selectable markers lacking their own promoters as a way to further enhance the frequency of obtaining homologous recombinants. In that way, the likelihood of the selectable marker being highly expressed upon integration into the genome will be much greater for homologous recombination events (where the promoterless gene will have been placed in the vicinity of the target gene promoter) than for random integration into the genome.

Target genes can also be modified by deletions. In the case of a deletion, the sequence to be deleted will be absent or removed from the corresponding targeting DNA and thus the "modification sequence" will constitute a missing sequence relative to the target DNA. The deletion will generally cover a portion of one or more exons and may include introns and flanking non-coding regions such as regulatory regions. The deletion may be as small as one base pair or as large as tens of thousands of base pairs.

Another specific form of modification is the introduction of a new gene into the animal cell genome. By flanking the new gene with sequences substantially isogenic with target DNA in the host cell, it is possible to introduce the gene in a site-specific fashion at the targeted location. Using this approach, a gene from any source (e.g., bacterial, plant, animal) can be introduced into an animal cell to impart new characteristics to the cell or to allow the animal cell to produce desired polypeptides which can then be isolated from the animal or from its cells in vitro.

Another form of modification is the insertion of a marker gene in a region outside of but proximal to a gene of interest. This sort of modification results in the creation of a new linkage in the animal genome. For this approach, the precise function of a target sequence need not be known, so long as it is known to be associated with a particular trait. Selectable markers can be introduced into precise locations adjacent to desirable genes to facilitate selection of desirable traits that are otherwise not selectable in culture. This procedure is of value, for instance, in order to facilitate animal breeding programs. Segregation of the trait through successive generations can be tracked by growing cells on the appropriate selective medium. Thus, the time required to breed improved varieties can be shortened. As an example of this kind of approach, regions identified by RFLP analysis to be associated with complex traits can be targeted and cells containing the traits can be selected in culture.

The targeting DNA comprises a sequence in which the desired sequence modifications are flanked by DNA substantially isogenic with a corresponding target sequence in the genome to be modified. The substantially isogenic sequence is preferably at least about 97–98% identical with the corresponding target sequence (except for the desired sequence modifications), more preferably at least about 99.0–99.5% identical, most preferably about 99.6 to 99.9% identical. Particularly for non-inbred animals (e.g., other than mice strains 129 and BALB/c), the sequencers are typically 100% identical. The targeting DNA and the target DNA preferably share stretches of DNA at least about 75 base pairs that are perfectly identical, more preferably at least about 150 base pairs that are perfectly identical, even more preferably at least about 500 base pairs that are perfectly identical. Accordingly, it is preferable to use targeting DNA derived from cells as closely related as possible to the cell line being targeted; more preferably, the targeting DNA is derived from cells of the same cell line as the cells being targeted. Most preferably, the targeting DNA is derived from cells of the same individual (or animal) as the cells being targeted.

Preferably, the targeting DNA sequence is at least about 100–200 bp of substantially isogenic DNA, more preferably at least about 300–1000 bp and generally less than about 15,000 bp. The amount of targeting DNA present on either side of a sequence modification can be manipulated to favor either single or double crossover events, both of which can be obtained using the present invention. In a double crossover or "replacement-type" event, the portion of the targeting DNA between the two crossovers will replace the corresponding portion of the target DNA. In a single crossover or "insertion-type" event, the entire targeting DNA will generally be incorporated into the target sequence at the site of the single crossover. To promote double crossovers, the modification sequences are preferably flanked by targeting DNA such that, upon linearization, the modification sequences are located towards the middle of the flanking targeting DNA. If single crossovers are desired, the targeting DNA should be designed such that the ends of the linearized targeting sequence correspond to target DNA sequences lying adjacent to each other in the genome, as described by Thomas, K., and M. Capecchi, *Cell* 51:503–512 (1987).

The DNA delivery molecule may contain only the targeting DNA with modification sequences or it may contain additional DNA flanking the targeting DNA. If this additional DNA contains a selectable marker, then it may be possible to further enrich for cells which have undergone double crossover homologous recombination because these cells will generally have lost the flanking selectable marker located outside the targeting DNA. Conversely, cells which have stably incorporated the flanking selectable marker are likely to have arisen by random integration of the DNA construct into the genome. One such flanking selectable marker is the HSV-tk gene which confers sensitivity to the antibiotic gancyclovir. Mansour, S., et al., *Nature* 336:348–352 (1988).

Combinations of selectable markers can also be used to advantage. For example, to target non-selectable gene "X," a neo gene (with or without its own promoter, as discussed above) can be cloned into a DNA sequence which is substantially isogenic with gene X. As discussed above, the placement of this marker gene, particularly whether it is in an exon or outside the coding sequence, will depend on the aim of the gene targeting. To use a combination of markers, the HSV-tk gene can be cloned such that it is outside of the targeting DNA (another selectable marker could be placed on the opposite flank, if desired). After introducing the DNA construct into the cells to be targeted, the cells can be selected on the appropriate antibiotics. In this particular example, those cells which are resistant to G418 and gancyclovir are most likely to have arisen by homologous recombination in which the neo gene has been recombined into gene X but the tk gene has been lost because it was located outside the region of the double crossover. As discussed above, it will be necessary to ensure that the selectable markers are adequately expressed in the recipient cells.

The targeting DNA construct may also contain replication systems which are functional in prokaryotes, especially *E. coli*, which were of use in constructing the DNA molecule, and for performing and analyzing genetic manipulations of the targeting sequence. Preferably, however, DNA sequence not required for the gene targeting is removed prior to introducing the DNA into cells to be targeted.

The DNA delivery molecule containing the targeting DNA may also contain DNA sequences or proteins that affect the uptake of the DNA delivery molecule or the fate of the molecule after introduction into the cells. For example, the DNA delivery molecule may be a viral capsid containing the targeting DNA, as discussed below. Also, the DNA delivery molecule may contain sequences or DNA binding proteins that affect degradation or localization of the molecule following entry into the targeted cells, or that affect the catalysis of homologous recombination.

Transformation of animal cells with the recombinant construct containing the targeting DNA can be carried out using essentially any method for introducing nucleotide sequences into animal cells including, as discussed below, microinjection, electroporation, calcium phosphate precipitation, and transfection using a virus or viral particle.

After the targeting DNA has been introduced into the animal cells, the cells in which the targeting DNA has stably integrated into the genome can be selected. The choice of which one to use will generally depend upon the nature of the sequence that has been integrated. For example, if the targeting DNA contains a selectable marker, as described above, then the integration of targeting DNA into the genome results in the stable acquisition of the selectable marker. In some situations the cells may be selected by virtue of a modification of the target gene. For example, if the target gene has a selectable phenotype, then modification of the target DNA may result in loss or alteration of that phenotype. In other situations, a selectable phenotype may result from juxtaposition of a DNA sequence present on the targeting DNA with DNA sequences present near the target DNA. For example, integration of a promoterless antibiotic resistance gene at the target site may result in expression of the resistance gene based on transcriptional activity at the target site.

It is also possible, although not essential, to use the polymerase chain reaction (PCR) to screen cells in which homologous integration has occurred. In an advantageous application, one PCR primer is directed to DNA in the modification sequence and another primer is directed to DNA near the target locus that is outside but proximal to the target DNA, such that integration results in the creation of a genomic DNA sequence in which the primer binding sites are facing each other in relative juxtaposition. After a number of rounds of amplification, DNA from such a locus will be present at much higher levels because it is being amplified exponentially rather than linearly.

Homologous recombination can be confirmed using standard DNA hybridization techniques, such as Southern blotting, to verify the presence of the integrated DNA in the desired genomic location.

Where the cells contain more than one copy of a gene, the cell lines obtained from the first round of targeting are likely to be heterozygous for the targeted allele. Homozygosity, in which both alleles are modified, can be achieved in a number of ways. One approach is to grow up a number of cells in which one copy has been modified and then to subject these cells to another round of targeting using a different selectable marker. Alternatively, homozygotes can be obtained by breeding animals heterozygous for the modified allele, according to traditional Mendelian genetics. In some situations, it may be desirable to have two different modified alleles. This can be achieved by successive rounds of gene targeting or by breeding heterozygotes, each of which carries one of the desired modified alleles.

The present invention can be used with a variety of cell types derived from a number of animal sources. As discussed above, the invention is especially useful with animals, such as non-murine animals, in which inbreeding is not very common. The choice of particular cell types for targeting will generally depend on the purposes for which the site-directed mutagenesis is undertaken. For example, if whole animals carrying a particular mutation are desired, then embryonic stem cells derived from that animal can be targeted and later introduced into blastocysts for growing the modified cells into chimeric animals. For embryonic stem cells, either an embryonic stem cell line or freshly obtained stem cells may be used. The resulting chimeric animals can be bred in order to obtain non-chimeric animals in which the mutation has been transmitted through the germ line.

Another approach to creating genetically altered animals that can be used with the present invention is to modify zygotes directly. For mammals, the modified zygotes can be then introduced into the uterus of a pseudopregnant female capable of carrying the animal to term.

Besides altering organisms through germ-line modifications, gene targeting can also be used to modify somatic cells. Cells of interest for somatic gene targeting include hematopoietic cells, T-lymphocytes and other cells of the immune system, epithelial cells, endothelial cells, adrenal medulla cells, keratinocytes, fibroblasts, osteoblasts, osteoclasts, neurons, ganglion cells, retinal cells, liver cells, myoblast cells, and cells of the islets of Langerhans. Also of interest will be the stem cells which serve as the progenitors of the above cells and which may be an original progenitor cell or a progenitor cell that has already become dedicated to a particular cell lineage.

In addition to applications such as the production of transgenic animals and gene-therapy, the techniques of the present invention are also useful in expanding basic knowledge with respect to animal cell function. For example, the expression of altered forms of genes and their promoters can be analyzed without position effects because the gene is altered in situ; and the function of sequences whose purpose is unknown can be determined by inactivating the sequence and observing changes in cell function.

The following list of terms, intended to supplement the descriptions above, will be useful in understanding the present invention:

Target DNA sequence

The DNA to be modified by homologous recombination. The target DNA can be in any organelle of the animal cell including the nucleus and mitochondria and can be an intact gene, an exon or intron, a regulatory sequence or any region between genes.

Desired sequence modifications

Sequence changes that it would be desirable to introduce into the target DNA. These sequence modifications may include insertions, deletions or substitutions of DNA sequence, or any combination thereof, and may be as small as a single base pair or as large as tens of thousands of base pairs. Insertions include the insertion of entire genes which may be of animal, plant, prokaryotic or viral origin.

Targeting DNA sequence

A DNA sequence containing the desired sequence modifications and which is, except for the sequence modifications, substantially isogenic with the target DNA.

DNA delivery molecule

The molecule comprising at least the targeting DNA which is introduced into cells to be targeted.

Uninterrupted sequence identity

The length of a stretch of DNA sequence that is identically conserved between two homologous DNA sequences.

Average sequence identity

The percentage of DNA sequence that is identically conserved between two homologous DNA sequences. For example, if a first DNA sequence comprises 200 base pairs and a second sequence differs at two sites (e.g. a small insertion such as 4 nucleotides, and a small deletion), then the average sequence identity is about 99%.

Homologous DNA sequence or homologous DNA

DNA sequence that is at least about 70% identical with a reference DNA sequence. An indication that two sequences are homologous is that they will hybridize with each other under fairly stringent conditions (see, e.g., Maniatis or Sambrook, infra).

Isogenic or substantially isogenic DNA

DNA sequence that is identical with or nearly identical with a reference DNA sequence. Indications that two sequences are isogenic is that they will hybridize with each other even under the most stringent hybridization conditions (see, e.g. Maniatis or Sambrook, infra); and will not exhibit sequence polymorphisms (i.e. they will not have different sites for cleavage by restriction endonucleases). The term "substantially isogenic" refers to DNA that is at least about 97–99% identical with the reference DNA sequence, and preferably at least about 99.5–99.9% identical with the reference DNA sequence, and in certain uses 100% identical with the reference DNA sequence. Indications that two sequences are substantially isogenic is that they will still hybridize with each other under the most stringent conditions (see, Sambrook) and they will only rarely exhibit RFLPs or sequence polymorphisms (relative to the number that would be statistically expected for sequences of their particular length which share at least about 97–99% sequence identity).

Homologous recombination

The term "homologous recombination" refers to the process of DNA recombination based on sequence homology. The term embraces both crossing over and gene conversion. Cellular recombination enzymes are believed to be involved in the process of recognizing sequence identity between distinct nucleotide sequences. Three distinct types of homologous recombination have been distinguished based on the nature of the recombination substrates and the mechanisms believed to be involved in mediating recombination: "chromosomal recombination," "extrachromosomal recombination" and "gene targeting" (see definitions, infra).

Chromosomal recombination

Homologous recombination between two DNA sequences within a single chromosome ("intrachromosomal recombination") or recombination between chromosomes ("interchromosomal recombination"). A common example of interchromosomal recombination is the mitotic recombination between homologous chromosomes.

Extrachromosomal recombination

Homologous recombination between two DNA sequences neither of which are located on chromosomes. An example of extrachromosomal recombination is the recombination between two viruses transfected into a single recipient cell.

Gene targeting

Homologous recombination between two DNA sequences, one of which is located on a chromosome and the other of which is not.

Non-homologous or "random" integration

Any process by which DNA is integrated into the genome that does not involve homologous recombination. It appears to be a random process in which incorporation can occur at any of a large number of genomic locations.

Selectable marker

A gene, the expression of which allows cells containing the gene to be identified on a particular medium. A selectable marker can be one that allows a cell to proliferate on a medium that prevents or slows the growth of cells without the gene. Examples include antibiotic resistance genes and genes which allow an organism to grow on a selected metabolite. Alternatively, the gene can facilitate visual screening of transformants by conferring on cells a phenotype that is easily identified. Such an identifiable phenotype may be, for example, the production of luminescence or the production of a colored compound, or the production of a detectable change in the medium surrounding the cell.

Animal cell

A cell of a multicellular eukaryotic organism of, for example, the phyla chordata, echinodermata, coelenterata, annelida, and arthropoda. Preferably, the animal cells are from an animal belonging to the phylum chordata, more preferably the subphylum vertebrata. Most preferably, the animal cells are non-murine mammalian cells, including human cells.

EXPERIMENTAL

A. General Methods

Generally, the nomenclature and standard laboratory procedures with respect to recombinant DNA technology can be found in Maniatis, T. et al... *Molecular Cloning—A Laboratory Manual*, Cold Spring Harbor Laboratory, Cold Spring Harbor, N.Y. (1982) (hereinafter "Maniatis"); and now in Second Edition by Sambrook, J., et al. (1989) (hereinafter "Sambrook"). Other general references are provided throughout this document. The procedures therein are believed to be well known in the art, and are provided for the convenience of the reader. Maniatis, Sambrook, and the other general references are specifically incorporated herein by reference.

B. Preparation of the Targeting DNA

1.) Isolation of Isogenic DNA

The targeting DNA comprises a sequence in which the desired sequence modifications are flanked by DNA substantially isogenic with a corresponding target sequence in the genome to be modified. The targeting DNA can be constructed exclusively from genomic DNA, from cDNA, from synthetic DNA or from any combination of the above. The genomic DNA can be cloned from a library of genomic DNA fragments in a bacteriophage vector (e.g., lambda phage), in a plasmid vector (e.g., pBR322 derivative), or in a cosmid vector; using techniques well-known in the art of recombinant DNA. cDNA can, e.g., be prepared from a mRNA population which forms the basis of preparation of a cDNA library. Alternatively, synthetic DNA fragments can be prepared based upon knowledge of the nucleotide sequence of the target DNA.

2.) Modifying the Targeting DNA

Modification of the targeting DNA will depend on two basic considerations: firstly, what modifications are desired in the target DNA; secondly, whether selectable sequences should be included as an aid in isolating homologous recombinants.

In some situations, the modified targeting DNA will already be available. If for example, a mutant version of a particular gene is already available as a recombinant DNA construct, then the targeting DNA may be obtained from that source using standard cloning techniques. See, e.g., Sambrook. As discussed above, the efficiency of homologous recombination depends in part on the isogenicity of the targeting DNA and the target DNA. Where the modification is available in a different cell line than that being targeted, it may be preferable to clone the modification sequence out of the original DNA and into DNA sequence that is more nearly isogenic with the target DNA. In general, such cloning will be performed in prokaryotic organisms, using standard cloning techniques. Id.

If a targeting DNA with desired sequence modifications is not already available, then a fragment of substantially isogenic targeting DNA can be obtained and modified. Generally, the isogenic targeting DNA will be most easily modified after being cloned onto vectors that can be used in prokaryotic organism such as *E. coli*. If an appropriate fragment of isogenic targeting DNA is not already available, then a gene library of the cell line to be targeted can be prepared and screened for the desired sequence using techniques well known in the art. See, e.g., Sambrook. Once the targeting DNA is cloned, insertions, deletions and alterations of DNA sequences can be achieved by techniques well known in the art. See, Sambrook. If the sequence of the target DNA is known, it is also possible to obtain synthetic DNA fragments in which one or more of the base pairs are specifically altered, added or removed.

One particular type of modification is the insertion of a gene within the targeting DNA. As discussed above, it will often be advantageous to include a selectable marker as an insert to facilitate selection of recombinants. A wide variety of such markers are generally known and available; and can be readily cloned into a desired targeting DNA construct using well known techniques. See, e.g., Sambrook.

C. Construction of DNA Delivery Molecules

Typically, cloning of the targeting DNA will be performed in *E. coli*, and standard plasmids such as pUC and pBR322 derivatives can be used. In many cases, it will be possible to use these plasmid DNAs directly as DNA delivery molecules; but it is preferable to minimize the amount of extraneous DNA on the delivery molecule. Thus, DNA sequence that will not be involved in targeting or selection of homologous recombinants can be removed prior to introduction of the DNA into the recipient cells. Preferably, the DNA will be linearized by cutting with a restriction enzyme prior to introduction into the cell. See, Sambrook. Where biological methods of DNA introduction are used, such as a virus or viral capsid, the DNA delivery molecule will be tailored accordingly to the particular system. For example, particular viral capsids generally work most efficiently with DNA sequences that are within a particular size range.

As discussed above, the DNA delivery molecule containing the targeting DNA may also contain DNA sequences or proteins that affect the uptake of the molecule or the fate of the molecule after introduction into the cells. For example, the DNA delivery molecule may be a viral capsid containing the targeting DNA, as discussed below. Also, the DNA delivery molecule may contain sequences or DNA binding proteins that affect degradation or localization of the molecule following entry into the targeted cells or molecules that affect the catalysis of homologous recombination.

D. Cells to be Targeted

The present invention can be used with essentially any cell into which DNA can be introduced. As discussed in the following section, there are a variety of methods applicable for introducing DNA into animal cells. The choice of cell type will depend on the particular goal of the site-directed mutagenesis. For example, embryonic stem cells or zygotes may be targeted for generating modified animals; whereas both germ-line and somatic cells may be usefully targeted for gene therapy. The choice of cells may also affect (or be affected by) the choice of transformation technique, as discussed below. Growth and manipulation of the cells can be performed using standard procedures as described in Hogan, B., et al, *Manipulating the Mouse Embryo*, Cold Spring Harbor, N.Y. (1986).

E. Introduction of the DNA into the Cells

Any technique that can be used to introduce DNA into the animal cells of choice can be employed. Electroporation has the advantage of ease and has been found to be broadly applicable, but a substantial fraction of the targeted cells may be killed during electroporation. Therefore, for sensitive cells or cells which are only obtainable in small numbers, microinjection directly into nuclei may be preferable. Also, where a high efficiency of DNA incorporation is especially important, such as targeting without the use of a selectable marker (as discussed above), direct microinjection into nuclei is an advantageous method because typically 5–25% of targeted cells will have stably incorporated the microinjected DNA. Retroviral vectors are also highly efficient but in some cases they are subject to other shortcomings, as described by Ellis, J., and A. Bernstein, *Molec. Cell. Biol.* 9:1621–1627 (1989). Where lower efficiency techniques are used, such as electroporation, calcium phosphate precipitation or liposome fusion, it is preferable to have a selectable marker in the targeting DNA so that stable transformants can be readily selected, as discussed above. A variety of such transformation techniques are well known in the art, including:

(1.) Direct microinjection into nuclei:

Targeting constructs can be microinjected directly into animal cell nuclei using micropipettes to mechanically transfer the recombinant DNA. This method has the advantage of not exposing the DNA to cellular compartments other than the nucleus and of yielding stable recombinants at high frequency. See, Capecchi, M., *Cell* 22:479–488 (1980).

(2.) Electroporation:

The targeting DNA can also be introduced into the animal cells by electroporation. In this technique, animal cells are electroporated in the presence of DNA containing the targeting construct. Electrical impulses of high field strength reversibly permeabilize biomembranes allowing the introduction of the plasmids. The pores created during electroporation permit the uptake of macromolecules such as DNA. Procedures are described in, e.g., Potter, H., et al., *Proc. Nat'l. Acad. Sci. U.S.A.* 81:7161–7165 (1984); and Sambrook, ch. 16.

(3.) Calcium phosphate precipitation:

The targeting constructs may also be transferred into cells by other methods of direct update, for example, using calcium phosphate. See, e.g., Graham, F., and A. Van der Eb, *Virology* 52:456–467 (1973); and Sambrook, ch.16.

(4.) Liposomes:

Encapsulation of DNA within artificial membrane vesicles (liposomes) followed by fusion of the liposomes with the target cell membrane can also be used to introduce DNA into animal cells. See Mannino, R. and S. Gould-Fogerite, *BioTechniques*, 6:682 (1988).

(5.) Viral capsids:

Viruses and empty viral capsids can also be used to incorporate DNA and transfer the DNA to animal cells. For example, DNA can be incorporated into empty polyoma viral capsids and then delivered to polyoma-susceptible cells. See, e.g., Slilaty, S. and H. Aposhian, *Science* 220:725 (1983).

(6.) Transfection using polybrene or DEAE-dextran:

These techniques are described in Sambrook, ch.16.

(7.) Protoplast fusion:

Protoplast fusion typically involves the fusion of bacterial protoplasts carrying high numbers of a plasmid of interest with cultured animal cells, usually mediated by treatment with polyethylene glycol. Rassoulzadegan, M., et al., *Nature*, 295:257 (1982).

(8.) Ballistic penetration:

Another method of introduction of nucleic acid segments is high velocity ballistic penetration by small particles with the nucleic acid either within the matrix of small beads or particles, or on the surface, Klein, et al., *Nature*, 327, 70–73, 1987.

F. Selection for Integration Events

In some situations, the gene targeting event will itself result in a selectable phenotype, in which case the targeted cells can be screened directly for homologous recombination. For example, disrupting the gene hprt results in resistance to 6-thioguanine. In many cases, however, the targeting will not result in such an easily selectable phenotype and, if a low efficiency transformation technique such as calcium phosphate precipitation is being used, it is preferable to include in the targeting DNA construct a selectable marker such that the stable integration of the targeting DNA construct in the genome will lead to a selectable phenotype. For example, if the targeting DNA contains a neo gene, then selection for integrants can be achieved by selecting cells able to grow on G418.

The relative frequency of targeting to a gene may be further improved by using a selectable marker which lacks its own promoter, since the likelihood of adequate expression of the selectable marker is greater where integration into a gene has occurred than for integration into the large parts of the genome that are believed to be transcriptionally quiescent.

G. Isolation of Homologous Recombinants

Using the present invention, the frequency of homologous recombination relative to random integration into the genome is substantially improved. The frequency is typically improved by a factor of 5 to 10, 50 to 100 or 1000 or more depending upon the particular old, targeting sequencers and other parameters known by the skilled artisan. In some cases, it will be feasible to directly obtain cells in which homologous recombination at the target locus has occurred. For example, gene targeting may itself result in a readily selectable phenotype. Also, selectable markers in the targeting DNA can be employed which will be preferentially expressed upon integration into the target gene by homologous recombination. Another approach is to utilize the polymerase chain reaction to screen the cells for homologous recombinants. See, e.g., Zimmer, A., et al., *Nature*, Vol. 338, pp.150–153 (1989); and Joyner, A., et al., *Nature*, Vol. 338, pp. 153–156 (1989).

However, using the present invention, a relatively large fraction of the stable integrants will be correctly targeted to the gene of interest rather than incorporated at random sites throughout the genome. Accordingly, it will be feasible to obtain homologous recombinants without the necessity of employing any special selection protocols or carrying out PCR-based screening.

The standard approach for confirming that a cell has undergone a homologous recombination event is to isolate genomic DNA and perform a Southern hybridization analysis to demonstrate that genomic DNA fragments hybridizing with a labelled probe of the target DNA have been rearranged because of the modification of the target DNA. Southern hybridization is described in Sambrook and Maniatis. Given the high frequency of homologous recombination obtainable with the present invention, the targeted cells can be checked directly for homologous recombination.

H. Targeting Both Alleles of a Target Sequence

Where the cells contain more than one copy of a gene, the cell lines obtained from the first round of targeting are likely to be heterozygous for the targeted allele. Homozygosity, in which both alleles are modified, can be achieved in a number of ways. One approach, exemplified below, is to grow up a number of cells in which one copy has been modified and then to subject these cells to another round of targeting using a different selectable marker. Alternatively, homozygotes can be obtained by breeding animals heterozygous for the modified allele, according to traditional Mendelian genetics.

In some situations, it may be desirable to have two different modified alleles. This can be achieved by successive rounds of gene targeting or by breeding heterozygotes, each of which carries one of the desired modified alleles.

I. Production of Genetically Altered Animals

Embryonic stem cells which have been modified can be injected into the blastocoel of a blastocyst and grown in the uterus of a pseudopregnant female. In order to readily detect chimeric progeny, the blastocysts can be obtained from a different parental line than the embryonic stem cells. For example, the blastocysts and embryonic stem cells may be derived from parental lines with different hair color or other readily observable phenotype. The resulting chimeric animals can be bred in order to obtain non-chimeric animals which have received the modified genes through germ-line transmission. Techniques for the introduction of embryonic stem cells into blastocysts and the resulting generation of chimeric animals are well known (see e.g., Bradley, A. *Production and analysis of chimaeric mice*, pp. 113–151 in Robertson, E. (ed.), *Teratocarcinomas and Embryonic Stem Cells: A Practical Approach*, Oxford IRL Press (1987); and Hogan, B., et al, *Manipulating the Mouse Embryo*, Cold Spring Harbor, N.Y. (1986)).

Targeting DNA can also be introduced directly into a zygote nucleus using, for example, microinjection. Selectable markers and/or other aspects of the present invention can be employed and the zygotes can be grown into animals using techniques well known in the art. In the case of mammals, the targeted organism can be introduced into the uterus of a pseudo-pregnant female capable of carrying the developing animal to term.

J. Somatic Gene Therapy

Similarly, the methods described above can be employed for somatic gene therapy to, e.g., alter the expression of a gene, or correct a defective gene, or introduce a new gene in somatic cells of a human or other animal. The somatic cells are first modified, using the methods described above, and then introduced into the same or a different individual (see Friedman, *Science* 244:1275–1281).

EXAMPLE 1

Gene Targeting Using Isogenic Targeting Constructs.

A. Targeting constructs:

The target DNA selected was the retinoblastoma susceptibility gene (Rb) in mouse embryonic stem cells of line E14. The targeting DNA consisted of a 10.5 kb HpaI fragment of Rb sequence from around the 19th and 20th exons of the gene (see FIG. 1b).

Two different sources of Rb sequence were used for the targeting DNA. The 10.5 kb targeting DNA sequence was either isolated from a mouse strain 129-derived DNA library ("129Rb"), or a BALB/c-derived DNA library ("B/cRb"). Since the recipient embryonic stem cells were also derived from mouse strain 129 (Hooper, M., et al., *Nature* 326:292–295 (1987)), the 129Rb targeting DNA will be substantially isogenic with the target DNA. As discussed below, the B/cRb targeting DNA sequence is very similar to the 129Rb sequence but differs by about 0.5–1.0% (i.e. one sequence difference per 100–200 nucleotides).

The chosen sequence modification was disruption of the Rb gene coding sequence by insertion of the neomycin phosphotransferase (neo) gene into the 19th exon of the gene. The neo marker was derived from plasmid pMC1neo poly(A) (Thomas, K., and M. Capecchi, *Cell* 51:503–512 (1987)). A mutation present in the neo coding sequence and reducing its ability to confer G418 resistance was corrected (see Yenofsky, R., et al. *Proc. Nat'l Acad. Sci. USA* 87:3435–3439 (1990). The neo marker was flanked by 2.5 and 8.0 kb of Rb sequence. The resulting constructs, 129Rb-neo and B/cRb-neo are shown in FIG. 1b. The targeting DNA sequences were separated from flanking vector DNA by cleavage with a restriction enzyme followed by gel electrophoresis and purification by electro-elution.

B. Gene targeting

Embryonic stem cell line E14, derived from mouse strain 129, was grown on BRL conditioned medium (Hooper, M., et al., *Nature* 326:292–295 (1987)). Cells ($3 \times 10^7$) were mixed with 90 micrograms of targeting DNA (either 129Rb-neo or B/cRb-neo) in a volume of 600 microliters of PBS buffer and electroporated using a Biorad Gene pulser (0.8 kV, 3 micro F, electrode distance 0.4 cm). Cells were reseeded on 10-cm tissue culture dishes at a density of about $10^7$ cells per plate. G418 (200 micrograms/ml) selection was started after one day; after eight days, colonies were randomly picked and grown up for analysis.

C. Analysis

Figure 1B:
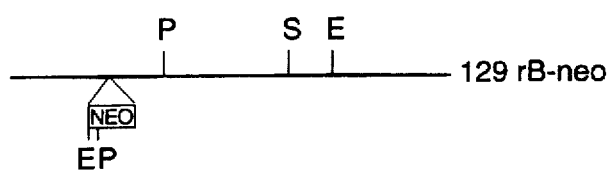

Double crossing-over at the Rb-locus will integrate the neo marker into the 19th exon of the Rb gene, thereby disrupting the coding sequence (FIG. 1a). G418-resistant colonies obtained from both electroporation experiments were analyzed by Southern hybridization. DNA from individual G418-resistant colonies was analyzed in the following way: 1–2×10$^6$ cells were embedded in 50 microliters of 05% of low melting point agarose in PBS buffer and incubated in 1 ml of EDTA (0.5M), Sarcosyl (1%) and Proteinase K (1 mg) for 48 h at 50° C. Agarose blocks were washed three times in Tris (10 mM), EDTA (10 mM), pH 8 plus PMSF (0.1 mM) and once in the appropriate restriction enzyme buffer. DNA digestion took place in 100 microliters of restriction enzyme buffer containing 50 units of restriction enzyme EcoRI for 6 hours at 37° C. Agarose blocks were melted at 65° C. and loaded onto 0.7% agarose gels for Southern analysis following standard procedures (see Maniatis or Sambrook). Using fragment A (FIG. 1b) as the hybridization probe, the non-modified Rb locus appears as a band of 9.7 kb (Rb); whereas integration of neo by homologous recombination gives a 4.9 kb band (neo).

D. Results

Although the targeting constructs 129Rb-neo and B/cRb-neo were identical, except for the origin of the Rb sequence, the results obtained with the two constructs were different. Using B/cRb-neo, 1 homologous recombinant was detected amidst 144 random integration events. In contrast, of 94 analyzed G418-resistant colonies obtained with 129Rb-neo, 33 underwent homologous recombination at one of the Rb alleles. Thus, gene targeting was about 45-fold more efficient with 129Rb-neo than with B/cRb-neo. The isogenic targeting construct allowed the easy recovery of homologous recombinants (1 out of 3 resistant colonies) without the use of any enrichment protocol.

Figure 2:
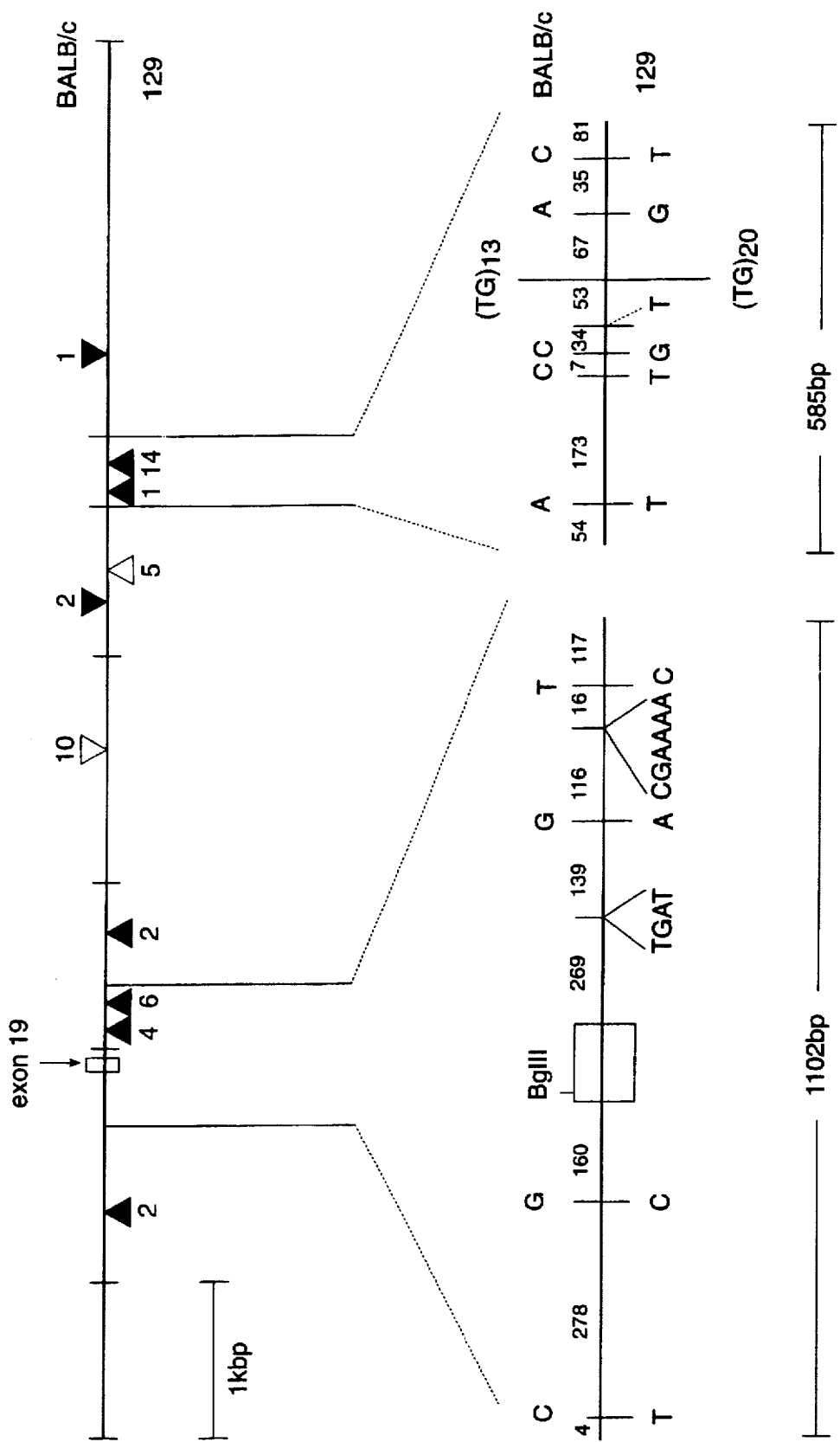
FIG. 2. Sequence divergence between BALB/c and 129 DNA at the region of homology. The upper part of the diagram represents the 10.5 kb Rb sequence present in targeting constructs B/cRb-neo and 129Rb-neo (see FIG. 1b). The sequence was divided into nine smaller fragments, as shown by the solid vertical lines. Filled triangles represent extra nucleotides within a fragment in the BALB/c-derived sequence (above the line) or within the 129-derived sequence (below the line). Open triangles indicate length differences within a fragment that could result from nucleotide insertions or restriction site polymorphisms. The lower part of the diagram shows nucleotide differences as determined by sequence analysis of the indicated regions.

E. Analysis of the sequence divergence between the 129 and BALB/c targeting DNAs A comparison of the 129-derived and the BALB/c-derived DNAs, ("129Rb" and "B/cRb," respectively) was made to confirm that even small amounts of sequence divergence can substantially affect the frequency of homologous recombination. The 10.5 kb Rb fragments present in targeting constructs 129Rb-neo and B/cRb-neo were separated into nine smaller fragments (as shown in FIG. 2). Two of these fragments fell into regions that were entirely sequenced. The remaining seven fragments were separated in a low melting point agarose gel, recovered from the gel, and digested with Hinf1, Taq1, or both, using standard techniques (see e.g., Sambrook, supra). The digested fragments were radioactively labelled and analyzed in a sequencing gel (see, id.).

The restriction digestion patterns of the two fragments were identical for 8 out of the 13 enzymes tested, showing that no gross alterations had occurred. Five restriction site polymorphisms were seen, suggesting that 5 base pair substitutions were present within the 275 basepairs (bp) analyzed in this way. Second, 1102 nucleotides around the site where the neo marker was inserted and 585 nucleotides 5 kb away from this site were sequenced. Within these two regions (containing 1687 nucleotides) nine basepair substitutions, three small deletions (1, 4 and 6 nucleotides) and a polymorphic CA-repeat (a 14 bp deletion) were detected in the BALB/c sequence with respect to the 129 sequence. The longest stretch of perfect homology within the sequenced region was 278 nt. Finally, to detect deletions/insertions in the remainder of the targeting constructs, the 10.5 kb Rb fragments were digested into 9 smaller fragments (see FIG. 2). Two of these fragments fell in the region already sequenced, the remaining seven were further digested with restriction enzymes, radioactively labelled and analyzed on a sequencing gel. By this analysis, 3 deletions (2, 2 and 5 nucleotides) and three small insertions (1, 2 and 10 nucleotides) were detected in the BALB/c fragment with respect to the 129 fragment. A summary of the sequence and restriction fragment length analyses is given in FIG. 2. Based on these results, we estimate that on the average one sequence difference (a base pair substitution or a deletion/insertion) was present per 160 nucleotides, for an overall sequence divergence in the range of about 0.5–1.0%. Thus, even though the two targeting constructs shared an average sequence identity of about 99%, they nevertheless exhibited a significant difference in their efficiency as gene targeting substrates.

EXAMPLE 2

Figure 1C:

Successive targeting using two different selectable markers, targeting a selectable marker A. First round of gene targeting The targeting construct contained a selectable marker, an hprt minigene, embedded in 17 kb of targeting DNA from the retinoblastoma susceptibility gene derived from mouse line 129 (see FIG. 1c). The cells to be targeted were the mouse embryonic stem cell line E14Tg2a, an HPRT-minus derivative of cell line E14 (which was derived from cell line 129; see Hooper, M., et al., Nature 326:292–295 (1987)). Cells were electroporated with targeting DNA as described in Example 2.

Integration of the hprt minigene into the ES cell genome results in the acquisition of the ability to grow on HAT medium. Of 35 tested colonies that were selected on HAT medium, 8 contained the hprt-minigene correctly integrated into the 19th exon of one of the Rb alleles via homologous recombination. None of the homologous recombinants contained additional hprt copies integrated elsewhere in the genome. One of these clones, designated HAT-20, was used as the recipient for a second targeting experiment.

B. Second round of gene targeting

Clone HAT-20 was subjected to gene targeting using the constructs 129Rb-neo and B/cRb-neo (described above in Example I). HAT-20 cells were electroporated with 90 micrograms of targeting constructs B/cRb-neo and 129Rb-neo and the linearized vector pMC1neo poly(A). G418$^R$ colonies were scored after 8 days; 6-Thioguanine (10 µg/ml) was added and surviving colonies were counted 8 days later. From each electroporation experiment individual colonies were picked and grown up for DNA analysis. Double crossing-over at the previously targeted Rb allele will substitute hprt for neo, giving colonies resistant to both G418 (neo+) and 6-Thioguanine (Hprt–). The ratio of homologous recombinants (resistant to both 6-TG and G418) to the total number of integrations (G418$^R$) was much higher with 129Rb-neo than with B/cRb-neo (see Table 1). Some 6-TG-resistant colonies were also seen after electroporation of HAT-20 with the plasmid pMC1neo poly(A), albeit at a much lower rate than with either targeting construct (Table 1).

DNA of individual clones (6-TG$^R$ and G418$^R$) was digested with PstI and analyzed by Southern hybridization. Using fragment A (FIG. 1b) as a probe, bands of the expected size appeared, corresponding to the wild type Rb allele (4.9 kb), the Rb allele containing hprt (7.7 kb) and the Rb allele containing neo (3.9 kb). Colonies resistant to both 6-TG and G418, obtained upon electroporation of HAT-20 with B/cRb-neo (a), 129Rb-neo (b) and pMC1neo poly(A) (c) were analyzed as described in Example I.

DNA analysis of 18 colonies obtained with 129Rb-neo confirmed that all 18 resulted from homologous recombination with the target allele. In contrast, analysis of the colonies obtained using the B/cRb-neo construct demonstrated that 14 out of 29 colonies resistant to 6-TG resulted from the spontaneous loss of the hprt containing allele rather than from homologous recombination. Analysis of colonies obtained using pMC1neo-poly (A) revealed that they had all lost the hprt containing Rb allele, possible by loss of the entire chromosome. Corrected for the spontaneous loss of the hprt minigene in the HAT-20 ES cell line, the frequency of homologous recombination was 1/200 for the B/cRb construct, but reached 1/10 using the isogenic targeting construct (129Rb). In summary, using isogenic DNA resulted in a 20-fold increase in the efficiency of gene targeting by homologous recombination.

TABLE 1

Efficiency of homologous recombination

| DNA | Number of cells (HAT-20) | G418$^R$ (total) | G418$^R$ & 6-TG$^R$ (HR) | Efficiency * (HR/total) |
|---|---|---|---|---|
| B/cRb-neo | 5 × 10$^7$ | 11500 | 105 | 1/200 |
| 129Rb-neo | 5 × 10$^7$ | 13500 | 1260 | 1/10 |
| PMC1neo p(A) | 2.5 × 10$^7$ | 5470 | 11 | — |

* Corrected number of homologous recombinants (HR) divided by total number of G418$^R$ colonies obtained. DNA analysis revealed that, in the case of B/cRb-neo, about half of the 6-TG$^R$ colonies resulted from spontaneous loss of the hprt allele rather than homologous recombination. The same was true for all of the colonies resulting from PMC1neo poly(A). For the isogenic construct (129Rb-neo), all of the colonies examined resulted from homologous recombination.

EXAMPLE 3

Targeting both alleles of a gene; and a comparison of positive/negative selection and isogenic targeting.

In the first step, the retinoblastoma (Rb) allele of mouse embryonic stem cell line E14 was disrupted by homologous recombination with a BALB/c-derived targeting construct employing a standard positive/negative selection strategy as described by Capecchi and co-workers (see Mansour, S., et al, Nature 336:348–352 (1988), and using approximately 18 kb of Rb targeting sequence, three correct integrations of a neo marker into the 19th exon of the Rb gene were isolated from a background of 3600 random integration events.

Figure 1D:
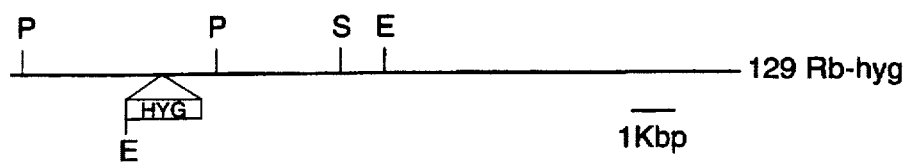

One of these single Rb knock-out cell lines was used as the recipient in a second electroporation experiment with an isogenic targeting construct, consisting of a hygromycin resistance gene (hyg) embedded in 17 kb of a 129-derived Rb sequence (see 129Rb-hyg, FIG. 1d). Electroporation conditions and DNA analysis were similar as described in the legend to FIG. 1. In a typical experiment, 8×10$^7$ cells were electroporated with 90 micrograms of 129Rb-hyg DNA (FIG. 1d). Hygromycin B (150 micrograms/ml) selection was started after one day. Approximately 15,000 hygromycin B resistant colonies were obtained and, after 12 days of growth, a number of individual colonies were picked and grown up for DNA analysis. DNA derived from 61 different Hygromycin B-resistant colonies was digested with EcoRI and analyzed by Southern hybridization. Using fragment B (FIG. 1d) as a probe, different sized bands, corresponding to the non-modified Rb allele (9.7 kb), the Rb allele with neo integrated (11.5 kb) and the Rb allele with hyg integrated (4.9 kb), could be observed. The Southern analysis revealed that approximately 75% of the Hygromycin B-resistant colonies tested (48 out of 61) resulted from homologous recombination. Thus, not only were homologous recombinants readily obtainable, they were the predominant type of cell arising from integration of the targeting DNA. Furthermore, all 48 of these lines had undergone homologous recombination at the Rb locus. In 40 of the lines, the hyg gene was correctly integrated into the remaining wild-type copy of the Rb gene thus giving cell lines in which both Rb alleles had been disrupted. In the other 8 lines, the hyg targeting DNA had incorporated by homologous recombination but the target had been the already modified allele in which the hyg targeting sequence replaced neo. By selecting the recombinants on both G418 and hygromycin, it is possible to select against cells in which the second targeting DNA has merely replaced the first.

The results also exemplify the effect of using isogenic targeting. With a fairly homologous targeting DNA, and employing a positive/negative selection strategy, less than 0.1% of the cells (approximately 1/1200) were homologous recombinants. In contrast, using isogenic targeting DNA, about 75% of the cells were correctly targeted without having to employ special selection techniques.

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

What is claimed is:

1. A method for modifying the genome of a target cell of a multicellular animal by homologous recombination between a target DNA sequence in the target cell genome and a targeting DNA molecule introduced into the cell, said method comprising:

a) constructing a targeting DNA molecule in which a desired sequence modification is contained in a targeting segment of DNA that is isogenic with the target DNA sequence in the target cell genome;

b) introducing said targeting DNA molecule into target cells; and c) isolating a target cell in which said targeting DNA molecule is incorporated into its genome following homologous recombination between said targeting DNA molecule and said target DNA sequence thereby modifying the cell genome of said of said target cell of said multicellular animal;

wherein the introducing step and the isolating step are performed in vitro, and further provided that where the target cell is an embryonic stem cell, the embryonic stem cell is murine.

2. A method according to claim 1, wherein the multicellular animal is a mammal.

3. A method according to claim 1, wherein the desired sequence modification in the targeting DNA segment comprises an insertion of a selectable marker.

4. A method according to claim 3, wherein the selectable marker is a gene conferring resistance to a compound inhibitory to cell growth.

5. A method according to claim 3 wherein the selectable marker is a gene conferring the ability to grow on a selected substrate.

6. A method according to claim 1, wherein the targeting DNA molecule is introduced into the cell by microinjection.

7. A method according to claim 1, wherein the target DNA is an immunoglobulin gene.

8. The method of claim 1 further comprising isolating the targeting segment of DNA, and incorporating the isolated targeting segment into the targeting construct.

9. The method of claim 8, wherein the targeting segment and the target cell are from the same inbred mouse strain.

10. The method of claim 9, wherein the targeting segment is from a strain 129 mouse and the target cell is from a strain 129 mouse.

11. In a method of in vitro gene targeting comprising introducing a targeting DNA construct bearing a desired DNA sequence modification into a target cell of a multicellular eukaryotic organism in vitro whereby the construct undergoes homologous recombination with a target DNA sequence in the genome of the target cell thereby introducing the desired sequence modification into the genome of said cell, the improvement comprising preparing said targeting DNA construct by introducing said desired DNA sequence modification into a targeting segment of DNA that is isogenic with the target DNA sequence in the target cell genome.

12. The method of claim 11 wherein the targeting segment of DNA is at least 1000 base pairs in length.

13. The method of claim 11 wherein the improvement further comprises the additional step of isolating said targeting segment of DNA is from a cell of the same multicellular eukaryotic organism from which the target cell is prepared.

14. The method of claim 11, wherein the multicellular eucaryotic organism is a noninbred animal.

15. The method of claim 11, wherein the multicellular euracyotic organism is a mammal.

16. The method of claim 11 further comprising isolating the targeting segment of DNA, and incorporating the isolated targeting segment into the targeting construct.

17. The method of claim 16 wherein the targeting segment and the target cell are from the same inbred mouse strain.

18. The method of claim 17, wherein the targeting segment is from a strain 129 mouse and the target cell is from a strain 129 mouse.

* * * * *